United States Patent [19]

Pächer et al.

[11] Patent Number: 5,344,317
[45] Date of Patent: Sep. 6, 1994

[54] ELECTRICALLY POWERED APPLIANCE FOR ORAL HYGIENE

[75] Inventors: Lothar Pächer, Mainz; Gustav Gassner, Kelkheim; Gottfried Voigt, Frankfurt am Main; Peter Hilfinger, Bad Homburg, all of Fed. Rep. of Germany

[73] Assignee: Braun Aktiengesellschaft, Frankfurt, Fed. Rep. of Germany

[21] Appl. No.: 855,703

[22] Filed: May 6, 1992

[30] Foreign Application Priority Data

Nov. 14, 1989 [DE] Fed. Rep. of Germany ....... 3937875

[51] Int. Cl.⁵ .................................... A61C 1/10
[52] U.S. Cl. ........................... 433/85; 433/80; 433/99; 433/100; 601/162
[58] Field of Search ............ 433/80, 85, 86, 99, 433/100; 128/66

[56] References Cited

U.S. PATENT DOCUMENTS

| | | | |
|---|---|---|---|
| 2,984,008 | 5/1961 | Weisberg | 433/100 |
| 3,449,831 | 6/1969 | Vandis | 433/100 |
| 4,363,626 | 12/1982 | Schmidt et al. | 433/85 |
| 4,619,612 | 10/1986 | Weber et al. | 433/80 |
| 5,197,458 | 3/1993 | Ito et al. | 128/66 |

FOREIGN PATENT DOCUMENTS

| | | |
|---|---|---|
| 0025456 | 3/1981 | European Pat. Off. . |
| 2238363 | 8/1972 | Fed. Rep. of Germany . |
| 3036781 | 8/1980 | Fed. Rep. of Germany . |
| 3101941 | 1/1981 | Fed. Rep. of Germany . |
| 3143196 | 10/1981 | Fed. Rep. of Germany . |
| 3420213 | 5/1984 | Fed. Rep. of Germany . |
| 3500085 | 1/1985 | Fed. Rep. of Germany . |
| 3601617 | 1/1986 | Fed. Rep. of Germany . |
| 1264138 | 2/1972 | United Kingdom . |

Primary Examiner—John J. Wilson
Attorney, Agent, or Firm—Fish & Richardson

[57] ABSTRACT

The present invention is directed to an appliance for oral hygiene, in particular an oral irrigating apparatus 10, comprising a hand-held unit 12 and a base unit 14 interconnected by a fluid conducting hose 19 and electrical conductors 21, 23. By means of an operating means 33 arranged on the handle section 28 of the hand-held unit 12, two operating parameters, particularly the On/Off state and the jet pressure of the oral irrigating apparatus 10, can be varied.

13 Claims, 3 Drawing Sheets

ELECTRICALLY POWERED APPLIANCE FOR ORAL HYGIENE

BACKGROUND OF THE INVENTION

This invention relates to an appliance for oral hygiene comprising a hand-held unit and a base unit, wherein the base unit accommodates an electrically powered device and the hand-held unit is connected to the base unit by means of electrical conductors. Arranged on the hand-held unit is an operating means for varying operating parameters of the electrically powered device. An oral hygiene appliance constructed in this manner is already known from DE-A1 30 36 781 (issued from the international application Publication No. WO 80/01873). Depending on the tool attached thereto, the hand-held unit of this known oral hygiene appliance is suitable for use as either a toothbrush or a water jet, being connected to the base unit by means of a hose having at least three electrical conductors embedded in the hose wall. Depending on whether a toothbrush or a jet attachment is affixed to the hand-held unit, either a first driving mechanism for moving the electric toothbrush or a second driving mechanism for a pump producing a predetermined water pressure is actuated. By means of an operating means arranged on the hand-held unit, the oral hygiene appliance is adapted to be turned on or off.

Especially if the oral hygiene appliance is used as an oral irrigating apparatus, an actuator is conventionally required on the base unit enabling the pressure of the stream of water discharged from the nozzle to be adjusted to meet individual user requirements. As a rule, the user will adjust the jet pressure on the base unit to a setting suited to his or her personal or medical needs before starting the tooth cleansing action. However, during cleansing, the situation may frequently occur that the user is unable to dislodge stubborn food particles from the interproximal spaces at the predetermined pressure setting of the nozzle. The user is thus obliged to temporarily increase the jet pressure on the base unit, for example, by increasing the rotational speed of the pump, reducing it subsequently to a comfortable value after the stubborn food particles have been removed.

It is an object of the present invention to simplify a variation of operating parameters of the oral hygiene appliance in order to thus facilitate and improve the manipulation of the oral hygiene appliance. In particular, embodiments of the present invention are aimed to permit an adjustment of operating parameters of the oral hygiene appliance by means of single-hand control of an operating means provided on the hand-held unit of the oral hygiene appliance. It is a further object to provide an operating means that is easy to clean for its special usage in oral hygiene appliances and is of high reliability in operation. Finally, it is desirable to provide a minimum possible number of electrical conductors between the hand-held unit and the base unit of the oral hygiene appliance. Particularly when the present invention is employed in oral irrigating apparatus in which the electrical conductors are preferably accommodated in the wall of the water supply hose between the base unit and the hand-held unit, the use of a minimum possible number of electrical conductors affords advantages in respect of manufacture, durability and cost of the electrically conducting hose.

SUMMARY OF THE INVENTION

The principal object of the present invention is accomplished by an appliance for oral hygiene incorporating the features initially referred to, in which the operating means provides two switching functions capable of varying a respective operating parameter. This ensures in an extremely advantageous manner that the user is in a position to control at least two device functions by actuating the operating means on the hand-held unit with a single hand. For example, one of the two controls, particularly the slide switch, may be used for turning the appliance on or off, while in oral irrigating apparatus, for example, the non-locking pushbutton is actuable to vary the jet pressure to a predetermined value departing from the basic setting for the duration of actuation of the non-locking pushbutton. It will be understood that operating parameters other than the jet pressure of the oral hygiene appliance including, for example, the pulse rate of a stream of water discharged from the oral irrigating apparatus, may be varied as, for example, the rotational speed of a rotary toothbrush, the angle of rotation of an oscillating toothbrush, or other operating conditions of the oral hygiene appliance. In any event, the operator is enabled to vary several, that is, at least two parameters using an operating means on the hand-held unit of the oral hygiene appliance.

Because the operating means is configured as a plate structure conformed to the curvature of a casing wall of the hand-held unit and guided along the casing wall and is provided with parallel slotted apertures extending over a partial area of the plate structure, an extremely straightforward construction of the operating means is provided affording ease of cleaning and operation. Because an area between the apertures is associated with the non-locking pushbutton and a resilient tongue integrally formed with the plate structure is associated with the slide switch, an operating means capable of performing at least two functions is provided which has the combined attributes of high robustness, ease of manufacture and assembly, and quick cleaning. While the one function is actuable by displacing the slide switch, the other function is actuable by pushing the non-locking pushbutton provided by the resilience of the plate structure intermediate the two slots. By providing for actuation of the switching contacts of a first switch by means of displacement of the slide switch between two positions, while the switching contacts of a second switch are actuable by means of the non-locking pushbutton only if the slide switch is in one of its two positions, it is advantageously ensured that the second operating parameter is variable by the non-locking pushbutton only if the first operating parameter determined by the switch position of the slide switch has a predetermined value. This arrangement prevents the non-locking pushbutton from modifying an operating parameter while the slide switch is in the Off position. The manipulation of the oral hygiene appliance is appreciably simplified by this embodiment, so that also children are in a position to maneuver the appliance without problems. Because one control is provided to turn the appliance on and off and a further control is provided to adjust the device to a predetermined maximum operating power, the present invention is advantageously embodied in the form of an oral irrigating apparatus. For example, an actuation of the non-locking pushbutton enables the jet pressure of the oral irrigating apparatus to be increased to a predetermined upper value in order to dislodge stubborn debris between or on the teeth. On release of the non-locking pushbutton, the jet pressure returns automatically to a value preset by the user on the base unit. Because the base unit is connected to the hand-held unit by means of only two electrical conductors or other, in particular optical, conductors, which in oral irrigating apparatus are conventionally routed within the walls of the hose to transport the cleansing agent from the base unit to the hand-held unit, the manufacture of the electrically conducting hose and thus also of the oral hygiene appliance is materially simplified. Moreover, the fail-safe capability of the appliance is increased because a reduction of the electrical or optical connecting means between the hand-held unit and the base unit reduces also the possibility of faults, in particular an open-circuit fault. Because an actuation of the operating means is converted into potential variations of control lines for controlling the On/Off condition and, respectively, for varying a set point of the operating power of the device, electrical means for implementation are introduced which are of an extremely straightforward construction and insusceptible to fault. The use of a discriminator function between at least one control line and one of the electrical conductors advantageously ensures that an actuation of the respective operating means selects only that particular control line which is associated with the controls, in particular the slide switch or the non-locking pushbutton. Finally, an application of the present invention particularly to an oral irrigating apparatus proves very advantageous, because a single-hand control on the hand-held unit of the oral irrigating apparatus enables several operating parameters of the oral irrigating apparatus to be varied. Further advantages of the present invention will become apparent from the subsequent description of embodiments in conjunction with the accompanying drawings.

DESCRIPTION OF THE DRAWINGS

In the drawings,

FIG. 2 a is a longitudinal sectional view of the casing of the hand-held unit of the oral irrigating apparatus and FIG. 2b is a corresponding side view showing the casing only in the area of the operating means.

DESCRIPTION OF THE PREFERRED EMBODIMENTS

Figure 1:
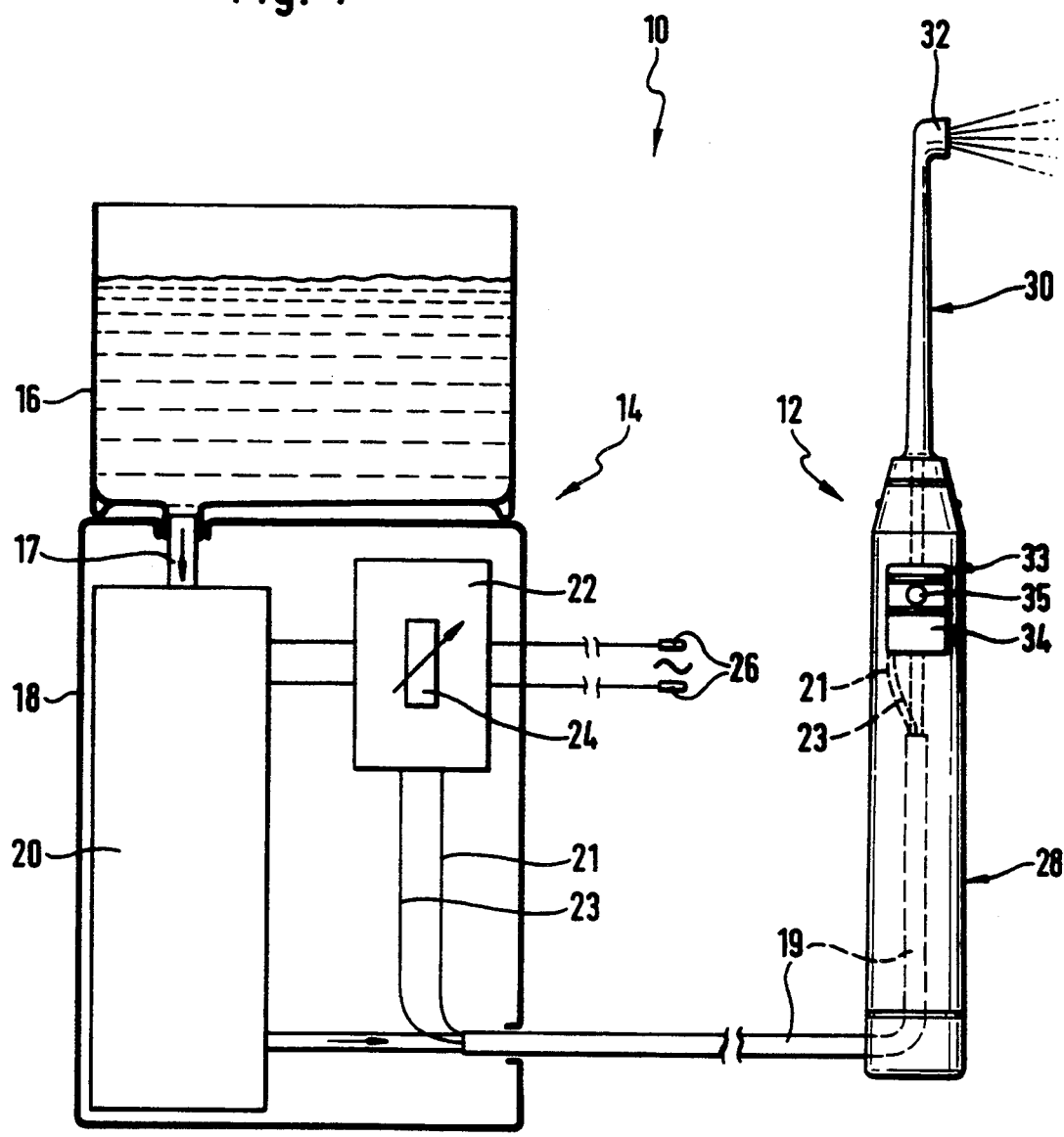
FIG. 1 is a diagrammatic view of an oral irrigating apparatus.

Referring now to the drawings, there is shown an oral irrigating apparatus 10 comprising a hand-held unit 12 and a base unit 14. From a water reservoir 16 seated on top of the base unit 14, water is admitted through an inlet conduit 17 to a pump unit 20 arranged in a housing 18 of the base unit 14. Water is discharged from the pump unit 20 through a hose 19 leading to the hand-held unit 12. Provided in the housing 18 is an electrical control system 22 for open or closed loop control of the pump unit 20 comprising a pump and an electric motor. The control system 22 is user-adjustable to a predetermined set point indicative of the jet pressure of the oral irrigating apparatus by means of a schematically shown actuation device 24 provided on the base unit 14. A supply connection 26 connects the base unit 14 to an electricity supply. Embedded in the wall of the hose 19 are two electrical or optical or other conductors 21, 23 having their one ends connected to the control system 22 in the base unit 14 while their other ends are connected to a switching unit 44 (FIG. 2) in the handle section 28 of the hand-held unit 12. Adapted to be coupled to the handle section 28 is a jet attachment 30 having a nozzle 32 adapted to discharge the fluid delivered to the hand-held unit 12 through the hose 19. An operating means 33 is slidably arranged on the handle section 28. Whilst the operating means 33 is comprised of a slide switch 34 and an integral non-locking pushbutton 35, it will be understood that it may also be embodied in other forms, as a toggle switch, rocker switch, or the like.

Figure 2:
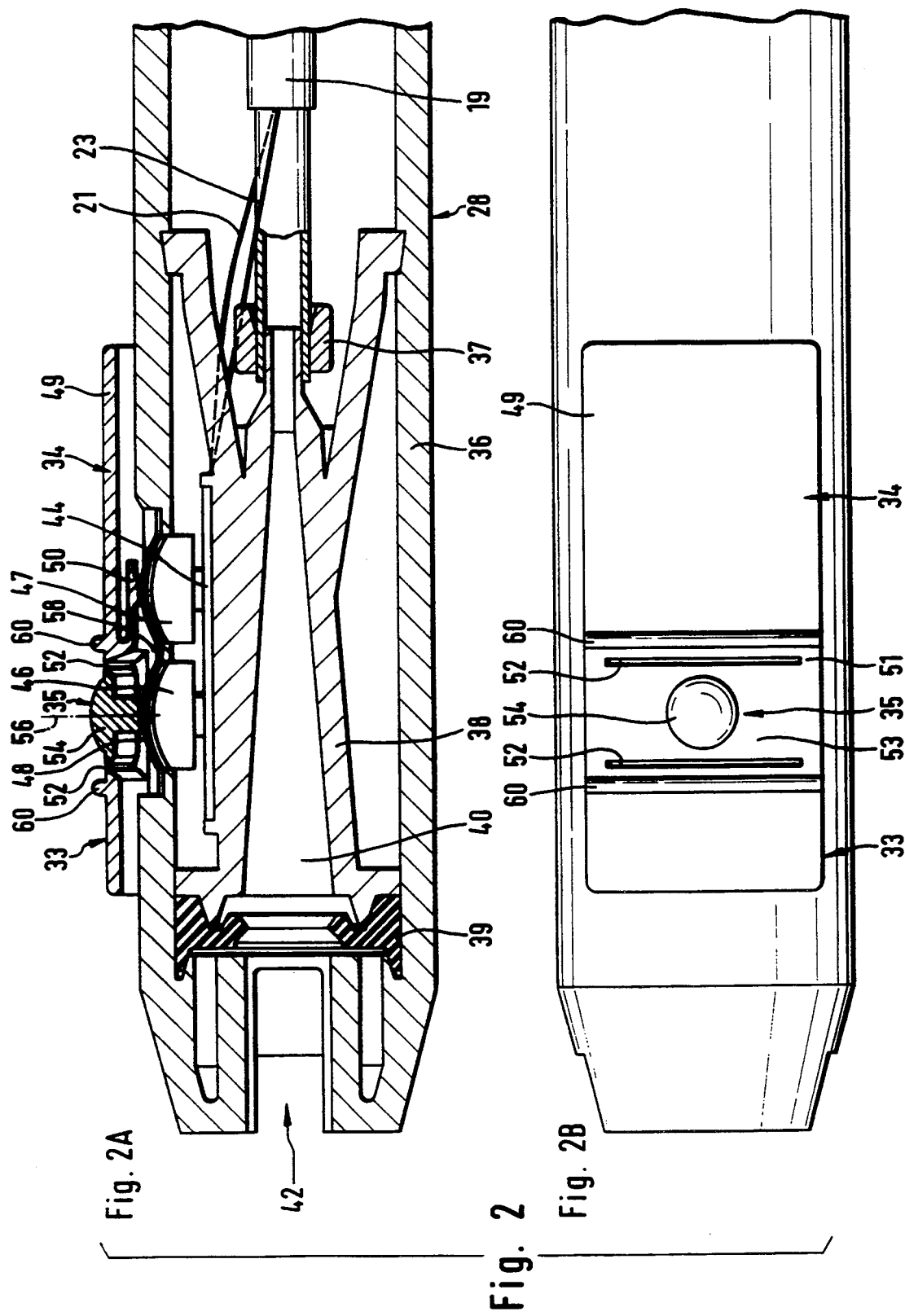

Details with regard to the structure and the function of the operating means will become apparent from FIG. 2. The handle section 28 substantially comprises a casing with a casing wall 36 receiving in its interior a casing insert 38. The hose 19 is secured to a neck of the casing insert 38 by means of a clamping structure 37. A central aperture 40 of the casing insert 38 terminates in the area of a ring seal 39 at the head end of the handle section 28. At this end, coupling means 42 are provided for coupling the jet attachment 30 with the handle section 28.

A switching unit 44 is affixed to the casing insert 38 opposite two plungers 46, 47 received in openings in the casing wall 36. In the present embodiment, the switching unit is made by thick-film technology. However, it will be understood that any type of electric switch may be used, including in particular microswitches, provided their size matches the available space. The plungers 46 and 47 serve to actuate the contacts of two switches 62 and 64 (FIG. 3) of the switching unit 44. The plungers 46 and 47 are guided by the side walls of the openings in the casing wall 36. A foil 48 connected to the casing wall 36 so as to be impervious to contaminants and humidity extends over and above the plungers 46 and 47. The foil 48 seals the casing in the area of the plungers 46 and 47, thus preventing the entrance of contaminants or humidity in the interior of the handle section 28. The operating means 33 is slidably mounted on the casing wall 36 above the plungers 46, 7. The fastening means for locating the operating means 3 in position on the casing wall 36 of the handle section 28 are not illustrated in greater detail in the Figures. For example, noses or tangs integrally formed on the underside of the operating means 33 may be provided for locking engagement with guide grooves in the casing wall 36, or other conventional fastening methods may be selected.

Figure 3:
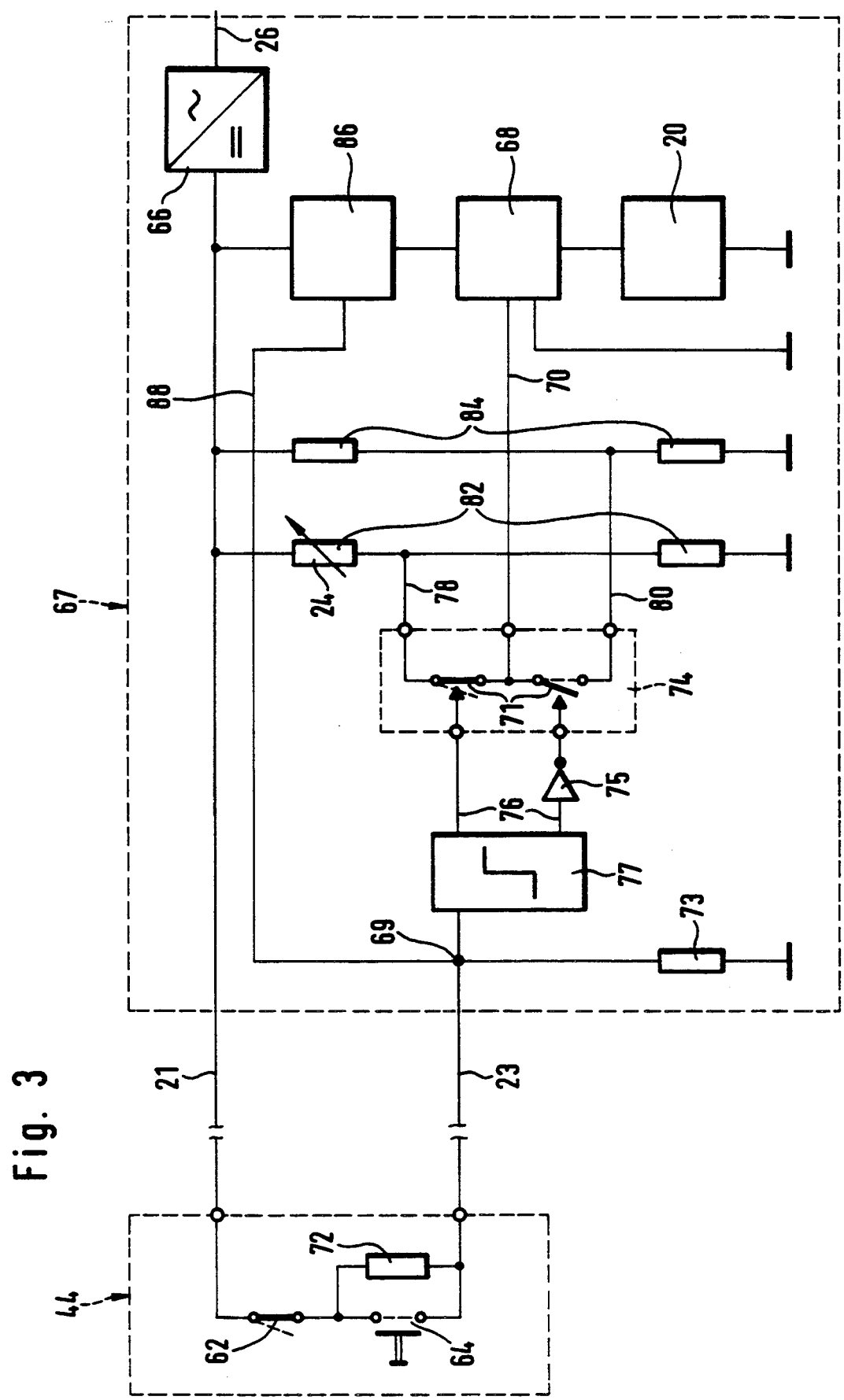
FIG. 3 is a block diagram to explain the principle of function of the electrical devices of the oral irrigating apparatus.

The operating means 33 is configured as an approximately rectangular plate structure 49 conformed to the curvature of the casing wall 36. Formed integrally with the underside of the plate structure 49 is a resilient tongue 50 which in the On position of the operating means 33 shown acts centrally on the plunger 47 as well as on the associated switch 62 (FIG. 3). This part of the operating means 33 referred to as a slide switch 34 for actuating the switch 62 serves to turn the oral irrigating apparatus 10 on and off.

Between two transverse rib members 60 provided on the plate structure 49 to facilitate the manipulation of the operating means 33, two apertures 52 are provided extending parallel to the transverse rib members 60. The apertures 52 do not extend over the entire cross dimensions of the plate structure 49, terminating rather in an edge area 51 of the plate structure 49. The area between the apertures 52 forms a surface in the form of a strip 53 having resilient properties. To facilitate actuation of the non-locking pushbutton 35 formed by the strip 53, a button-shaped protrusion 54 is provided in the center of the strip 53. The application of pressure to the non-locking pushbutton 35 actuates the plunger 46 and thus the switch 64 (FIG. 3) of the switching unit 44. However, the switch 64 is actuable only if the slide switch 34 is in the On position illustrated in FIG. 2. In the Off position in which the operating means 33 is displaced in the direction of the foot end of the handle section 28 until a central axis 56 of the non-locking pushbutton 35 is in the mid-area 58 intermediate the plungers 46 and 47, an actuation of the switch 64 by the non-locking pushbutton 35 is prevented from occurring. In the Off position of the operating means 33, the tongue 50 of the slide switch 34 lies on the side adjacent to the plunger 47, causing opening of the switch 62 and turning the oral irrigating apparatus 10 off.

The mode of operation of the arrangement is as follows:

To energize the oral irrigating apparatus 10, the operating means 33, that is, the slide switch 34 is moved to the On position, causing, as shown in FIG. 2, the tongue 50 to actuate the switch 62 (FIG. 3) through the plunger 47 and to activate the pump unit 20, as will be explained in greater detail in the following with reference to FIG. 3. In dependence upon the setting of the actuation device 24, the pump unit 20 will propel liquid at a pressure suited to meet the individual user's needs to the nozzle 32 on the handle section 28 from which it is discharged as a jet. If the user considers it necessary to vary the pressure of the cleansing jet, for example, to increase it to remove stubborn food particles in the interproximal spaces, he or she may actuate the non-locking pushbutton 35 to increase the pressure of the cleansing jet to a predetermined, particularly maximum, value, which will be maintained as long as the non-locking pushbutton 35 is actuated. After the stubborn food particles are successfully dislodged, the user will stop pressing down on the non-locking pushbutton 35, causing the pressure of the water jet to return automatically to the value preselected with the actuation device 24. Thus, the operating means 33 of the present invention, in addition to being adapted to turn the oral irrigating apparatus 10 on and off, enables an operating parameter to be varied over a shorter or longer period of time, involving in the present embodiment in particular an increase in the jet pressure of the oral irrigating apparatus 10, which is accomplished by single-hand control of the operating means 33 on the hand-held unit 12. Clearly, this function may also be performed by two separate controls 34, 35 provided on the hand-held unit 12.

The configuration of the electric circuit of the two switches 62 and 64 of the switching unit 44 actuable by the slide switch 34 and the non-locking pushbutton 35 will be explained in the following with reference to the block diagram of FIG. 3. A particular aspect of this circuit configuration resides in the fact that the electrical connection between the hand-held unit 12 and the base unit 14 is established by just two electrical conductors 21, 23 while yet allowing a variation of at least two operating parameters involving the On/Off state parameter and the jet pressure or operating power parameter of the pump unit. The circuit configuration is comprised of two parts, including the switching unit 44 accommodated in the handle section 28 and comprising the switches 62 and 64, wherein a resistor 72 is connected in parallel with switch 64, and the electric circuit 67 provided in the base unit 14. The two units are interconnected electrically by means of conductors 21 and 23 and mechanically through the hose 19. To supply a dc voltage, the electric circuit 67 includes a rectifier 66 adapted to be connected to an ac source of voltage by a supply connection 26. The output potential of rectifier 6 is applied to the one contact of switch 62 through the electrical conductor 21. Switch 62, switch 64 and a resistor 73 combine in this sequence to form a series circuit having its base point applied to a reference potential, in particular frame potential. By arranging resistor 72 in parallel with switch 64, the potential of the electrical conductor 23 branching off from the switch 64 or of a reference point 69 inside the circuit 67 varies as follows: With the switch 62 open—which corresponds to the Off state of the oral irrigating apparatus 10—frame potential will reside at reference point 69, irrespective of whether switch 64 is open or closed. Closing of switch 62 with switch 64 open causes the potential across reference point 69 to assume such values as are determined by the ratio of the voltage division produced by resistors 72 and 73. If switch 64 is closed with switch 62 being equally closed, resistor 72 will be bypassed, causing the potential across reference point 69 to be increased to a maximum value determined by the output potential of rectifier 66. The value determined by the ratio of the voltage division of resistors 72, 73 as well as any higher value at reference point 69 is sufficient to turn on a standby unit 86 which is connected to reference point 69 through a control line 88 and actuates in turn a control system 68 and the pump unit 20 connected thereto. The control system 68 receives the set point of the pumping power through a set point signal line 70. This set point is adjusted by the ratio of the voltage division of a voltage divider 82 to which the supply voltage is applied. One of the resistors of the voltage divider 82 is formed by a variable resistor, that is, the actuation device 24. In dependence upon the setting of the actuation device 24 which is individually adjustable by the user on the base unit 14, the output pressure of the pump unit 20 and thus the pressure of the jet discharged from the nozzle 32 may be set at specific values agreeable to the user. The set point signal is applied to the input of a first switch 71. The input of a second switch 71 is connected to the center tap of a second voltage divider 84 equally receiving the supply voltage. While a variable set point is adjustable with the first voltage divider 82, the second voltage divider 84 is dimensioned such as to supply a fixed set point corresponding, for example, to an approximately maximum pumping power and thus a maximum jet pressure. The outputs of the two switches 71 are connected together for onward transmission to the control system 68 through the set point signal line 70. The switches 71 are, for example, part of an analog multiplexer 74 and may be electrically driven to the On/Off state by control lines 76. By inserting an inverter 75 in one of the two control lines 76, the two switches 71 are driven in complementary fashion, causing only one of the two switches 71 to be closed at a time, the other switch being open. A discriminator or comparator function 77 is provided between the electrical conductor 23 and the control lines 76. The internal operating point of the comparator function 77 is assigned a logic level such that it switches its digital output state or the potential of the control lines 76 from 1 to 0 or vice versa if the value of the input potential across reference point 69 increases from the value predetermined by the ratio of the voltage division of resistors 72 and 73 to the value of the supply voltage. This potential jump occurs at reference point 69 precisely when the non-locking pushbutton 35 actuates switch 64 while switch 62 is closed. If only switch 62 is closed, the potential level of the control lines 76 causes the signals of a signal line 78 connected to the center tap of the voltage divider 82 to be applied to the set point signal line 70 through one of the switches 71. Closing of switch 64 increases the potential across reference point 69 to the level of the supply voltage, and the control lines 76 are switched over in complementary fashion by means of the comparator function 77. In this event, the signal line 80 connected to the center tap of the voltage divider 84 is connected to the set point signal line 70. It follows from this description that, with switch 62 closed, the set point signal line 70 receives different set points in dependence upon the position of switch 64, which set points are determined by the ratio of the voltage division of voltage dividers 82 and 84. The set point determined by voltage divider 84 corresponds particularly to a maximum value of the pumping power or jet pressure, which comes to bear if switch 64 is actuated by means of non-locking pushbutton 35 with the appliance in turned-on condition. With switch 64 open, the pumping power or the jet pressure is determined by the ratio of the voltage division of the variable voltage divider 82 which is variable by means of the actuation device 24 on the base unit 14. It will be understood that the voltage dividers 82, 84 may also be supplied with the motor voltage, in which event the set point becomes dependent on the rotational speed of the motor and a control of the motor speed is made possible.

It will be recognized that the present invention is not limited to the specific application to oral irrigating apparatus and may find usage in any appliance for oral hygiene requiring an adjustment of two operating parameters by single-hand control. The electronic circuitry proves advantageous particularly if it is necessary or advisable to provide a minimum possible number of electrical conductors between a hand-held unit and a base unit of an oral irrigating apparatus. A minimum number of electrically conducting connections is necessary for reasons of operational reliability and, in the present example, the rather complex arrangement of the electrical conductors in the side wall of a water-conducting hose.

We claim:

1. An oral irrigating appliance with a base unit with a pump unit for delivering a liquid and an electrical control of said pump unit, said appliance comprising a hand-held unit, and a hose and electrical conductors connecting said hand-held unit to said base unit, said hand-held unit including a liquid outlet orifice and an operating means for varying the amount of liquid delivered by said pump unit, wherein said hand-held unit comprises a first switch and a second switch, both for operating said electrical control, wherein said first and second switches are operated by said operating means, wherein said first switch serves to turn said pump unit on and off and said second switch serves to adjust said pump unit to deliver the liquid at a specific predetermined maximum flow rate.

2. The oral irrigating appliance of claim 1 wherein said second switch is actuable by means of said operating means only if said operating means is in a position in which said pump unit is in its On condition brought about by said first switch.

3. The oral irrigating appliance of claim 2 wherein said operating means is integrally formed, providing a slide switch and a non-locking pushbutton.

4. The oral irrigating appliance of claim 3 wherein said operating means is configured as a plate structure conformed to the curvature of a casing wall of said hand-held unit, said plate structure being guided along said casing wall and being provided with opposite slotted apertures extending over a partial area of said plate structure.

5. The oral irrigating appliance of claim 4 wherein said non-locking pushbutton is located in an area between said apertures of said plate structure, and said slide switch includes a resilient member for operating said first switch.

6. The oral irrigating appliance of claim 1, 2, or 3 wherein said first and second switches each includes switching contacts and wherein the switching contacts of said first switch are operated by displacement of said slide switch between two positions, and wherein the switching contacts of said second switch (64) are operated by said non-locking pushbutton when said slide switch is in one of its two positions.

7. The oral irrigating appliance of claim 6 wherein said non-locking pushbutton operates on the operating power, overriding any other actuation device.

8. The oral irrigating appliance of claim 1 wherein said base unit is connected to said hand-held unit by two electrical conductors.

9. The oral irrigating appliance of claim 8 further comprising a control line carrying a potential that controls an On/Off state of the appliance and wherein the potential of said control line is varied by displacement of said slide switch.

10. The oral irrigating appliance of claim 8 further comprising internal switches that vary a set point of the operating power of the appliance and a control line carrying a potential that determines a condition of said internal switches, wherein the potential of the control line is varied by pushing said non-locking pushbutton.

11. The oral irrigating appliance of claim 10 further comprising a comparator function connecting one of said two electrical conductors to said control line.

12. An oral irrigating appliance comprising a base unit with a pump unit for delivering a liquid and an electrical control of said pump unit, and a hand-held unit connected to said base unit by means of a hose and two conductors, said hand-held unit including a liquid outlet orifice and an operating means for varying the amount of liquid delivered by said pump unit, said operating means on said hand-held unit including circuitry for turning said oral irrigating apparatus on and off and to temporarily adjust the jet pressure of said oral irrigating appliance to a predetermined upper value deviating from a standard value.

13. The oral irrigating appliance of claim 12 wherein the jet pressure of said oral irrigating apparatus is adjustable to the upper value by said operating means independent of the adjustment of any other actuation device for operating on the jet pressure.

* * * * *